(12) United States Patent
Yamada et al.

(10) Patent No.: US 8,558,045 B2
(45) Date of Patent: Oct. 15, 2013

(54) CATALYST FOR AROMATIZATION OF LOWER HYDROCARBONS AND PROCESS FOR PRODUCTION OF AROMATIC COMPOUNDS

(75) Inventors: Shinichi Yamada, Mishima (JP); Tomohiro Yamada, Numazu (JP); Yuji Ogawa, Kawagoe (JP); Takuya Hatagishi, Numazu (JP); Yo Yamamoto, Numazu (JP); Yoshio Sugiyama, Mishima (JP)

(73) Assignee: Meidensha Corporation, Tokyo (JP)

( * ) Notice: Subject to any disclaimer, the term of this patent is extended or adjusted under 35 U.S.C. 154(b) by 741 days.

(21) Appl. No.: 12/595,924

(22) PCT Filed: Mar. 28, 2008

(86) PCT No.: PCT/JP2008/056117
§ 371 (c)(1),
(2), (4) Date: Oct. 14, 2009

(87) PCT Pub. No.: WO2009/004843
PCT Pub. Date: Jan. 8, 2009

(65) Prior Publication Data
US 2010/0137666 A1 Jun. 3, 2010

(30) Foreign Application Priority Data

Jun. 29, 2007 (JP) .................................. 2007-172021
Jun. 29, 2007 (JP) .................................. 2007-172024
Jan. 17, 2008 (JP) .................................. 2008-007896
Jan. 17, 2008 (JP) .................................. 2008-007897
Feb. 20, 2008 (JP) .................................. 2008-038304

(51) Int. Cl.
*C07C 2/76* (2006.01)
(52) U.S. Cl.
USPC ........................................ 585/418; 585/420
(58) Field of Classification Search
USPC .................................................. 585/418, 420
See application file for complete search history.

(56) References Cited

U.S. PATENT DOCUMENTS

| | | | |
|---|---|---|---|
| 4,100,262 A | 7/1978 | Pelrine | |
| 4,543,347 A | 9/1985 | Heyward et al. | |
| 6,051,520 A | 4/2000 | Wu et al. | |
| 2010/0016647 A1 | 1/2010 | Yamada et al. | |

FOREIGN PATENT DOCUMENTS

| | | |
|---|---|---|
| JP | 7-000826 A | 1/1995 |
| JP | 10-024237 A | 1/1998 |
| JP | 10-128123 A | 5/1998 |
| JP | 10-272366 A | 10/1998 |
| JP | 11-60514 A | 3/1999 |
| JP | 2002-336704 A | 11/2002 |
| JP | 2004-269398 A | 9/2004 |
| JP | 2007-14894 A | 1/2007 |

OTHER PUBLICATIONS

Satoshi Kikuchi et al., Study on Mo/HZSM-5 Catalysts Modified by Bulky Aminoalkyl-Substituted Silyl Compounds for the Selective Methane-to-Benzene (MTB) Reaction, Journal of Catalysis, vol. 242, 2006, pp. 349-356.
S. Qi et al., "Methane aromatization using Mo-based catalysts prepared by microwave heating," Catalysis Today, vol. 98, No. 4, 2004, pp. 639-645.
USPTO Notice of Allowance, U.S. Appl. No. 12/524,029, Jun. 6, 2012, 7 pages.
Qun Dong et al., "Studies on Mo/HZSM-5 Complex catalyst for Methane Aromatization", Journal of Natural Gas Chemistry, vol. 13 (2004), pp. 36-40.
F. Solymosi et al., "Aromatization of Methane over Supported and Unsupported Mo-Based Catalysts", Journal of Catalysis, vol. 165 (1997), pp. 150-161.
Shinichi Yamada et al., USPTO Office Action, U.S. Appl. No. 12/524,029 Oct. 20, 2011, 6 pages.
USPTO Office Action, U.S. Appl. No. 12/524,029, Feb. 24, 2012, 15 pages.

*Primary Examiner* — Thuan D Dang
(74) *Attorney, Agent, or Firm* — Foley & Lardner LLP

(57) ABSTRACT

A catalyst for aromatizing a lower hydrocarbon, in order to increase the amount of production of useful aromatic compounds, such as benzene and toluene, by improving the methane conversion rate, the benzene formation rate, the naphthalene formation rate and the BTX formation rate (or a total formation rate of benzene, toluene and xylene) is such that molybdenum and silver are loaded on a metallosilicate as a substrate. It is more preferable to obtain the aromatizing catalyst by loading molybdenum and silver after modifying a zeolite formed of the metallosilicate with a silane compound that has a molecular diameter larger than a pore diameter of the zeolite and that has an amino group, which selectively reacts at a Bronsted acid point of the zeolite, and a straight-chain hydrocarbon group.

7 Claims, 7 Drawing Sheets

CATALYST FOR AROMATIZATION OF LOWER HYDROCARBONS AND PROCESS FOR PRODUCTION OF AROMATIC COMPOUNDS

TECHNICAL FIELD

The present invention relates to improvements in a catalyst for aromatizing lower hydrocarbons and in a process for producing aromatic compounds, and more specifically to advanced uses of natural gas, biogas and methane hydrate which contain methane as a main component. Natural gas, biogas and methane hydrate are regarded as effective energy resources against global warming, and therefore an interest in techniques using them has grown. A methane resource is expected to be a novel organic resource in the next generation or to be a hydrogen resource for use in fuel cells, by putting a clean property of methane to full use. The present invention particularly relates to: a chemical and catalytic conversion technique for efficiently producing, from methane, a high purity hydrogen and aromatic compounds containing benzenes, naphthalene and the like which are materials of chemical products such as plastics; and a process for producing the catalyst.

As a process for producing hydrogen and aromatic compounds such as benzene from methane, one where methane is reacted in the presence of a catalyst is known. In such a process, it is generally said that molybdenum loaded on a ZSM-5 zeolite is effectively used as the catalyst (as disclosed in Non-Patent Document 1). However, even in the case of using such a catalyst, there are problems of serious carbon formation and low methane conversion rate.

For example in Patent Documents 1 to 3, catalysts capable of solving the above problems are proposed, the catalyst being formed loading catalyst materials such as Mo (molybdenum) on a porous metallosilicate. It is confirmed from Patent Documents 1 to 3 that lower hydrocarbons are efficiently converted into aromatic compounds thereby obtaining a high purity hydrogen by using a catalyst formed of a porous metallosilicate substrate having pores of 7 angstrom in diameter and loading a metal component thereon. According to the above Patent Documents, the substrate loads thereon the metal component exemplified by molybdenum, cobalt, iron and the like. Further, a catalyst for aromatizing lower hydrocarbons, as disclosed in Patent Document 4, is formed by modifying zeolite formed of metallosilicate with silane compounds and then loading molybdenum thereon. With this aromatizing catalyst, a rate of producing a certain aromatic compound such as benzene and toluene can be stabilized.

The catalyst formed of ZSM-5 loading molybdenum thereon has been considered to be effective in the process for reacting methane in the presence of the catalyst thereby producing hydrogen and aromatic compounds such as benzene from methane.

However, the carbon formation is still serious even with such a catalyst, so as to decline a catalytic performance in a short time. Additionally, there exists a problem that a methane conversion rate (or a ratio of methane used to produce aromatic compounds and hydrogen) is low. These problems are not sufficiently solved even with the catalysts as disclosed in Patent Documents 1 to 3, so that a further development in such catalysts is desired in order to further improve a production efficiency of aromatic compounds.

It is essential to increase the methane conversion rate in the use of the catalyst for reforming methane to benzene, and it is necessary for increasing the methane conversion rate to increase a reaction temperature applied when supplying methane gas. However, the catalysts as disclosed in Patent Documents 1 to 3 are largely lowered in catalytic activity life when the reaction temperature at which the catalysts are reacted with a feedstock gas is increased.

With the aromatizing catalyst as disclosed in Patent Document 4 a rate of producing aromatic compound can be stabilized, but a further development is desired in activity life stability of the methane conversion rate, a benzene formation rate, a naphthalene formation rate and a BTX formation rate (or a total formation rate of benzene, toluene and xylene) from the viewpoint of mass production of aromatic compounds.

Non-Patent Document 1: "JOURNAL OF CATALYSIS" 1997, vol. 165, pp. 150-161

Patent Document 1: Japanese Patent Provisional Publication No. 10-272366

Patent Document 2: Japanese Patent Provisional Publication No. 11-60514

Patent Document 3: Japanese Patent Provisional Publication No. 2004-269398

Patent Document 4: Japanese Patent Provisional Publication No. 2007-14894

DISCLOSURE OF THE INVENTION

Therefore, a catalyst for aromatizing a lower hydrocarbon to solve the above task is such that molybdenum and silver are loaded on a substrate formed of metallosilicate.

Furthermore, in a process for producing an aromatic compound to solve the above task, molybdenum and silver are loaded on a substrate formed of metallosilicate, thereby producing a catalyst; and the catalyst is reacted with a lower hydrocarbon and a carbonic acid gas, thereby producing the aromatic compound.

According to the catalyst for aromatizing a lower hydrocarbon or to the process for producing the aromatic compound, it is allowed to improve an activity life stability of the methane conversion rate, the benzene formation rate, the naphthalene formation rate and the BTX formation rate (or the total formation rate of benzene, toluene and xylene).

The above-mentioned metallosilicate is exemplified by ZSM-5, MCM-22 or the like. Further, it is preferable that a concentration of the loaded molybdenum after calcination is within a range of from 2 to 12% by weight relative to the substrate, while a mole ratio of the loaded silver to 1 mol of the molybdenum is within a range of from 0.01 to 0.3. With this, the improvement of the activity life stability can be ensured. Furthermore, the calcination is preferably made after loading the molybdenum and the silver on the metallosilicate at a temperature of from 400 to 700° C., with which the strength and property of the catalyst can be maintained.

In the above-mentioned process for producing the aromatic compound, the carbonic acid gas is added preferably in an amount ranging from 0.5 to 6% relative to a total amount of the reaction gas. With this, a produced amount of the aromatic compound (which is a useful component such as benzene and toluene) is stabilized.

Furthermore, the catalyst for aromatizing a lower hydrocarbon is a catalyst that produces an aromatic compound by being reacted with the lower hydrocarbon and a carbonic acid gas. The catalyst includes molybdenum, silver and zeolite formed of metallosilicate. The molybdenum and the silver are loaded on the zeolite after modifying the zeolite with a silane compound. The silane compound is larger than a pore of the zeolite in molecular diameter and has an amino group and a straight-chain hydrocarbon group. The amino group is able to selectively react with the zeolite at a Bronsted acid point of the zeolite.

Furthermore, in the process for producing an aromatic compound to solve the above task, the process including the steps of (a) modifying zeolite formed of metallosilicate with a silane compound larger than a pore of the zeolite in molecular diameter, the silane compound having an amino group and a straight-chain hydrocarbon group, the amino group being able to selectively react with the zeolite at a Bronsted acid point of the zeolite; (b) loading molybdenum and silver on the zeolite thereby producing a catalyst; and (c) reacting the catalyst with a reaction gas containing a lower hydrocarbon and a carbonic acid gas, thereby producing the aromatic compound.

According to the aromatizing catalyst formed in such a manner as to load molybdenum and silver on the substrate after modifying the substrate with the silane compound and according to the process for producing the aromatic compound by using the aromatizing catalyst, it is allowed to improve the activity life stability of the methane conversion rate, the benzene formation rate, the naphthalene formation rate and the BTX formation rate (or the total formation rate of benzene, toluene and xylene). The carbonic acid gas to be reacted with the catalyst may be replaced with carbon monoxide gas.

The metallosilicate to be treated with the silane compound is exemplified by a porous metallosilicate formed with pores of 4.5 to 6.5 angstrom in diameter, such as ZSM-5 and MCM-22.

An example of the silane compound is APTES (3-aminoproxyl-triethoxysilane). The APTES is added for modifying the zeolite with the silane compound, preferably in an amount of less than 2.5%, for example in an amount of 0.5% by weight relative to the total amount of the catalyst which has undergone calcination. With this, the activity life stability of the methane conversion rate, the benzene formation rate, the naphthalene formation rate and the BTX formation rate (or the total formation rate of benzene, toluene and xylene) can be reliably improved.

It is preferable that the molybdenum is loaded on the metallosilicate modified with the silane compound in an amount ranging from 2 to 12% by weight relative to a total amount of the catalyst which has undergone calcination, and that a mole ratio of the loaded silver to 1 mol of the molybdenum is within a range of from 0.01 to 0.8. With this, the activity life stability of the methane conversion rate, the benzene formation rate, the naphthalene formation rate and the BTX formation rate can be reliably improved.

Additionally, the calcination is made after loading the molybdenum and the silver on the metallosilicate modified with the silane compound, preferably at a temperature of from 550 to 800° C.

In the process for producing the aromatic compound by using the aromatizing catalyst on which molybdenum and silver are loaded after the calcination, it is preferable that the carbonic acid gas is added in an amount ranging from 0.5 to 6% relative to a total amount of the reaction gas. With this, the activity life stability of the methane conversion rate, the benzene formation rate, the naphthalene formation rate and the BTX formation rate can be reliably improved. The carbonic acid gas excessively insufficient in amount (or less than 0.5%) reduces an oxidizing action on the precipitated coke so as to lower the activity life stability, while that in an excessive amount (or an amount of not less than 6%) causes a direct oxidation reaction of methane gas, thereby producing an excessive amount of hydrogen and carbon monoxide. With this, a methane gas concentration required for reaction is lowered so as to reduce the amount of production of benzene. In view of the above, in the present invention the carbonic acid gas is added in an amount ranging from 0.5 to 6% relative to a total amount of the reaction gas thereby efficiently stabilizing the methane conversion rate, the benzene formation rate, the naphthalene formation rate and the BTX formation rate.

With the catalyst for aromatizing lower hydrocarbons and the process for producing aromatic compounds according to the present invention, it is allowed to improve the activity life stability of the methane conversion rate, the benzene formation rate, the naphthalene formation rate and the BTX formation rate. It is, therefore, made possible to increase the amount of production of useful aromatic compounds such as benzene and toluene.

BEST MODE FOR CARRYING OUT THE INVENTION

Figure 1:
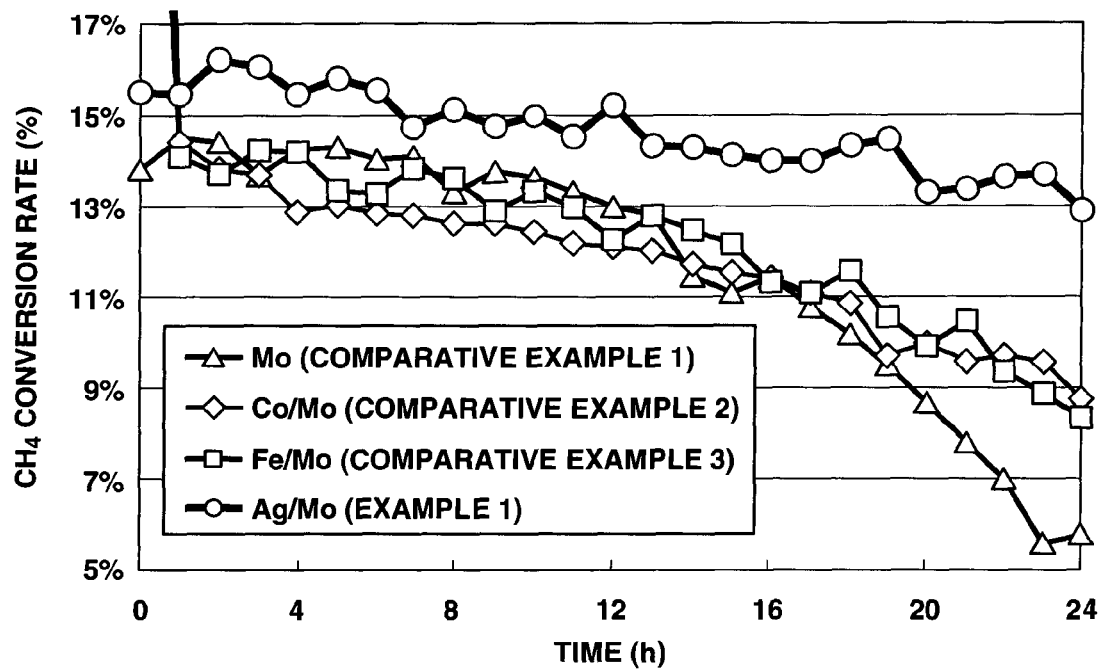
FIG. 1 shows time variations in methane conversion rate, the time variations being provided concerning catalysts of Comparative Example 1 (loading Mo singly), Comparative Example 2 (loading Co and Mo in one process step), Comparative Example 3 (loading Fe and Mo in one process step) and Example 1 (loading Ag and Mo in one process step), respectively, in which each of the catalysts was reacted with methane gas and carbonic acid gas.

The catalyst for aromatizing lower hydrocarbons according to an embodiment of the invention includes at least one of molybdenum and a compound thereof, and is to be reacted with carbonic acid gas (carbon dioxide) in addition to the lower hydrocarbons when producing aromatic compounds.

In a first embodiment of a catalyst for aromatizing lower hydrocarbons, a substrate on which a metal component is to be loaded substantially includes a porous metallosilicate formed with pores of 4.5 to 6.5 angstrom in diameter. On the metallosilicate, molybdenum is loaded as a first metal component while silver is loaded as the other metal component than the first metal component (i.e., as a second metal component). The molybdenum and silver components can be loaded on the metallosilicate by adding the metallosilicate to an impregnation solution prepared with silver acetate or silver nitrate and ammonium molybdate and by drying and calcining the metallosilicate which has been impregnated with the molybdenum and silver components.

Thus, the first embodiment of the catalyst according to the present invention is not formed loading MoC (molybdenum carbide) or the molybdenum component alone but formed loading silver in addition to molybdenum, as the second metal component, so as to provide the catalyst with the stability. Particularly, the activity life stability is improved in terms of the methane conversion rate, the benzene formation rate, the naphthalene formation rate and the BTX formation rate (or a total formation rate of benzene, toluene and xylene).

A second embodiment of a catalyst for aromatizing a lower hydrocarbon is formed including molybdenum, silver and zeolite formed of metallosilicate. The molybdenum and the silver are loaded after modifying the zeolite with a silane compound larger than a pore of the zeolite in molecular diameter and having an amino group and a straight-chain hydrocarbon group, the amino group being able to selectively react with the zeolite at a Bronsted acid point of the zeolite.

When producing aromatic compounds, the first and second embodiments of the catalyst according to the present invention are reacted with a reaction gas containing lower hydrocarbons and carbonic acid gas. The carbonic acid gas is added in an amount ranging from 0.5 to 6% relative to a total amount of the reaction gas.

In the second embodiments, a substrate on which the metal components are loaded substantially includes a porous metallosilicate formed with pores of 4.5 to 6.5 angstrom in diameter. The molybdenum and silver components can be loaded on a metallosilicate by adding the metallosilicate modified with silane to an impregnation solution prepared with silver acetate or silver nitrate and ammonium molybdate and then by drying and calcining the metallosilicate which has been impregnated with the molybdenum and silver components. An example of a silane compound used in the modification with silane (or in the silane-modification) is APTES (3-aminoproxyl-triethoxysilane). The APTES is added such that the silane compound has an amount of less than 2.5%, more specifically 0.5% by weight relative to the total amount of the catalyst which has undergone calcination.

Thus, the second embodiment of the catalyst according to the present invention is formed by loading the molybdenum and silver components on the metallosilicate which has been modified with the silane compound. With this, the catalyst can obtain the stability. Particularly, the activity life stability is improved in terms of the methane conversion rate, the benzene formation rate, the naphthalene formation rate and the BTX formation rate (or a total formation rate of benzene, toluene and xylene).

A catalyst for aromatizing lower hydrocarbons which catalyst is used for a process for producing aromatic compounds according to the present invention will be explained with reference to the following Examples.

1. Production of Catalyst for Aromatizing Lower Hydrocarbons

Comparative Example 1

In Comparative Example 1, ZSM-5 ($SiO_2/Al_2O_3$=25 to 60) of ammonium type was employed as metallosilicate, on which molybdenum was singly loaded.

(1) Composition

Composition of inorganic component: ZSM-5 (82.5 wt %), clay (12.5 wt %), and glass fiber (5 wt %)

Total composition: the above-mentioned inorganic component (76.5 wt %), an organic binder (17.3 wt %), and water content (24.3 wt %)

(2) Shaping Process

The inorganic component, the organic binder and the water content were prepared to have the above-mentioned composition and mixed or kneaded by a means of kneading (or a kneader). Subsequently, the thus mixed substance was formed into a rod (5 mm in diameter and 10 mm in length) by a vacuum extrusion machine. The extrusion pressure applied during this shaping process was set within a range of from 2 to 8 MPa.

Normally, the catalyst substrate applied in hydrocarbon reforming is used as a fluidized bed catalyst in the form of particles having a particle diameter of from several to several hundreds of micrometers. Such a catalyst substrate is produced by mixing a catalyst substrate material with an organic binder, an inorganic binder (e.g., clay in general) and water thereby obtaining slurry, and then by pelletizing the slurry by spray drying (free from shaping pressure), followed by calcination. In this case where there is no shaping pressure, the amount of clay added as a calcination assistant in order to ensure a calcination velocity is within a range of from about 40 to 60 wt %. However, in the present invention in which the catalyst is shaped by the vacuum extrusion machine, i.e. by a high-pressure shaping, it is allowed to reduce the amount of additives such as clay to a range of from 15 to 25 wt %. With this, the catalytic activity can be improved.

(3) Impregnation with Molybdenum

The shaped substance obtained by the above-mentioned shaping process was added to a stirred ammonium molybdate solution so as to be impregnated with a molybdenum component, followed by drying and calcining processes as will be discussed. The shaped substrate was added such that molybdenum was in an amount of 6 wt % relative to the ZSM-5.

(4) Drying and Calcining Process

Drying was carried out at 70° C. for 12 hours and then further carried out at 90° C. for about 36 hours, thereby removing the water content added in the shaping process. Thereafter, calcination was conducted at temperature-increasing and temperature-decreasing rates both of which range from 90 to 100° C./h. In order to remove the organic binder added in the shaping process but not to instantaneously calcine it, about 2 to 6 hours of temperature retention within a temperature range of from 250 to 500° C. was performed twice. If the temperature-increasing and temperature-decreasing rates exceed the above-mentioned rate and if the retention time enough to remove the binder is not ensured, the binder is to calcine instantaneously so as to decrease the strength of the calcined substance. A calcination temperature was set within a range of from 550 to 800° C. This was because the calcination temperature of not higher than 550° C. decreases the strength of the substance while that of not lower than 800° C. causes a property reduction. In Comparative Example 1, the calcination was conducted at 550° C. in air for 5 hours.

(5) Carburization Treatment

The above-mentioned calcined substrate was increased in temperature to 700° C. within 2 hours under the flow of a mixture gas of $CH_4$ and $H_2$ (a mixture ratio $CH_4/H_2$ was 1/4) and kept in this condition for 3 hours. Thereafter, the atmosphere was replaced with a reaction gas formed of $CH_4$ and increased in temperature to 780° C., thereby obtaining a catalyst of Comparative Example 1.

Comparative Example 2

A procedure of Comparative Example 1 (including the processes as discussed in (1) Composition, (2) Shaping process, (4) Drying and Calcining Process and (5) Carburization Treatment) was repeated with the exception that the impregnation process was carried out in such a manner as to load cobalt in addition to molybdenum, thereby obtaining a catalyst of Comparative Example 2.

In the impregnation process, an impregnation solution was prepared with cobalt acetate and ammonium molybdate. The shaped substance obtained in the shaping process was added to the impregnation solution with stirring so as to be impregnated with a molybdenum component and a cobalt component, and then subjected to evaporation to dryness. This substance was then calcined in air at 550° C. for 5 hours thereby obtaining a catalyst on which molybdenum and cobalt were loaded. A loaded amount of the molybdenum was 6% by weight relative to the ZSM-5, while a mole ratio of the loaded cobalt to the molybdenum was 0.3:1.0.

Comparative Example 3

A procedure of Comparative Example 1 (including the processes as discussed in (1) Composition, (2) Shaping process, (4) Drying and Calcining Process and (5) Carburization Treatment) was repeated with the exception that the impregnation process was carried out in such a manner as to load iron in addition to molybdenum, thereby obtaining a catalyst of Comparative Example 3.

In the impregnation process, an impregnation solution was prepared with iron acetate and ammonium molybdate. The shaped substance obtained in the shaping process was added to the impregnation solution with stirring so as to be impregnated with a molybdenum component and an iron component, and then subjected to evaporation to dryness. This substance was then calcined in air at 550° C. for 5 hours thereby obtaining a catalyst on which molybdenum and iron were loaded. A loaded amount of the molybdenum was 6% by weight relative to the ZSM-5, while a mole ratio of the loaded iron to the molybdenum was 0.3:1.0.

Example 1

A procedure of Comparative Example 1 (including the processes as discussed in (1) Composition, (2) Shaping process, (4) Drying and Calcining Process and (5) Carburization Treatment) was repeated with the exception that the impregnation process was carried out in such a manner as to load silver in addition to molybdenum, thereby obtaining a catalyst of Example 1.

In the impregnation process, an impregnation solution was prepared with silver acetate and ammonium molybdate. The shaped substance obtained in the shaping process was added to the impregnation solution with stirring so as to be impregnated with a molybdenum component and a silver component, and then subjected to evaporation to dryness. This substance was then calcined in air at 550° C. for 5 hours thereby obtaining a catalyst on which molybdenum and silver were loaded. A loaded amount of the molybdenum was 6% by weight relative to the ZSM-5, while a mole ratio of the loaded silver to the molybdenum was 0.3:1.0.

Example 2

A procedure of Comparative Example 1 (including the processes as discussed in (1) Composition, (2) Shaping process, (4) Drying and Calcining Process and (5) Carburization Treatment) was repeated with the exception of the size of the shaped substance and the impregnation process, thereby obtaining a catalyst of Example 2 on which silver and molybdenum were loaded in a mole ratio of 0.6:1.0.

In the shaping process, the mixed substance obtained in Comparative Example 1 from the inorganic component, the organic binder and the water content was formed into a rod having a diameter of 2.4 mm and a length of 5 mm by a vacuum extrusion machine at an extrusion pressure of from 2 to 8 MPa. In the impregnation process, an impregnation solution was prepared with silver acetate and ammonium molybdate. Then, the shaped substance which had undergone the shaping process and formed of the ZSM-5 was added to the impregnation solution with stirring, so as to be impregnated with a molybdenum component and a silver component. This substance was calcined in air at 550° C. for 5 hours upon being dried, thereby obtaining a ZSM-5 substrate on which molybdenum and silver were loaded. In preparation of the above-mentioned impregnation solution, a loaded amount of the molybdenum was set to be 6% by weight relative to a total amount of the catalyst which had undergone calcination while a mole ratio of the loaded silver to the molybdenum was set to be 0.6:1.0.

Example 3

A procedure of Comparative Example 1 (including the processes as discussed in (1) Composition, (2) Shaping process, (4) Drying and Calcining Process and (5) Carburization Treatment) was repeated with the exception of the size of the shaped substance and the impregnation process, thereby obtaining a catalyst of Example 3 on which silver and molybdenum were loaded in a mole ratio of 0.8:1.0.

In the shaping process, the mixed substance obtained in Comparative Example 1 from the inorganic component, the organic binder and the water content was formed into a rod having a diameter of 2.4 mm and a length of 5 mm by a vacuum extrusion machine at an extrusion pressure of from 2 to 8 MPa. In the impregnation process, an impregnation solution was prepared with silver acetate and ammonium molybdate. Then, the shaped substance which had undergone the shaping process and formed of the ZSM-5 was added to the impregnation solution with stirring, so as to be impregnated with a molybdenum component and a silver component. This substance was calcined in air at 550° C. for 5 hours upon being dried, thereby obtaining a ZSM-5 substrate on which molybdenum and silver were loaded. In preparation of the above-mentioned impregnation solution, a loaded amount of the molybdenum was set to be 6% by weight relative to a total amount of the catalyst which had undergone calcination while a mole ratio of the loaded silver to the molybdenum was set to be 0.8:1.0.

Example 4

A procedure of Comparative Example 1 (including the processes as discussed in (1) Composition, (2) Shaping process, (4) Drying and Calcining Process and (5) Carburization Treatment) was repeated with the exception of the size of the shaped substance and the impregnation process, thereby obtaining a catalyst of Example 4 on which silver and molybdenum were loaded in a mole ratio of 0.1:1.0.

In the shaping process, the mixed substance obtained in Comparative Example 1 from the inorganic component, the organic binder and the water content was formed into a rod having a diameter of 2.4 mm and a length of 5 mm by a vacuum extrusion machine at an extrusion pressure of from 2 to 8 MPa. In the impregnation process, an impregnation solution was prepared with silver acetate and ammonium molybdate. Then, the shaped substance which had undergone the shaping process and formed of the ZSM-5 was added to the impregnation solution with stirring, so as to be impregnated with a molybdenum component and a silver component. This substance was calcined in air at 550° C. for 5 hours upon being dried, thereby obtaining a ZSM-5 substrate on which molybdenum and silver were loaded. In preparation of the above-mentioned impregnation solution, a loaded amount of the molybdenum was set to be 6% by weight relative to a total amount of the catalyst which had undergone calcination while a mole ratio of the loaded silver to the molybdenum was set to be 0.1:1.0.

Example 5

A procedure of Comparative Example 1 (including the processes as discussed in (1) Composition, (2) Shaping process, (4) Drying and Calcining Process and (5) Carburization Treatment) was repeated with the exception of the size of the shaped substance and the impregnation process, thereby obtaining a catalyst of Example 5 on which silver and molybdenum were loaded in a mole ratio of 0.3:1.0.

In the shaping process, the mixed substance obtained in Comparative Example 1 from the inorganic component, the organic binder and the water content was formed into a rod having a diameter of 2.4 mm and a length of 5 mm by a vacuum extrusion machine at an extrusion pressure of from 2 to 8 MPa. In the impregnation process, an impregnation solution was prepared with silver acetate and ammonium molybdate. Then, the shaped substance which had undergone the shaping process and formed of the ZSM-5 was added to the impregnation solution with stirring, so as to be impregnated with a molybdenum component and a silver component. This substance was calcined in air at 550° C. for 5 hours upon being dried, thereby obtaining a ZSM-5 substrate on which molybdenum and silver were loaded. In preparation of the above-mentioned impregnation solution, a loaded amount of the molybdenum was set to be 6% by weight relative to a total amount of the catalyst which had undergone calcination while a mole ratio of the loaded silver to the molybdenum was set to be 0.3:1.0.

Example 6

A procedure of Example 5, including the catalyst composition and the size of the shaped substance was repeated with the exception that silver and molybdenum were loaded in a mole ratio of 0.3:1.0 after modifying the shaped substance formed including ZSM-5 with a silane compound, thereby obtaining a catalyst of Example 6.

In a process for modifying the substrate with silane (a silane-modification process), APTES was employed as a silane compound. The APTES was added to and dissolved in ethanol, with which the shaped substance formed including ZSM-5 which had undergone the shaping process as discussed in Comparative Example 1 was impregnated for a certain period of time, such that the APTES was in an amount of 0.5% by weight relative to a total amount of the catalyst which has undergone calcination. This substance was calcined in air at 550° C. for 6 hours upon being dried, thereby modifying the shaped substance with the silane compound.

In the impregnation process, an impregnation solution was prepared with silver acetate and ammonium molybdate. The shaped substance which had undergone the silane-modification process was added to the impregnation solution with stirring so as to be impregnated with a molybdenum component and a silver component. Thereafter, the shaped substance was dried and then calcined in air at 550° C. for 5 hours thereby obtaining a ZSM-5 substrate on which molybdenum and silver were loaded. In preparation of the above-mentioned impregnation solution, a loaded amount of the molybdenum was 6% by weight relative to a total amount of the catalyst, while a mole ratio of the loaded silver to the molybdenum was 0.3:1.0.

2. Evaluation of Catalysts of Comparative Examples and Examples

Figure 13:
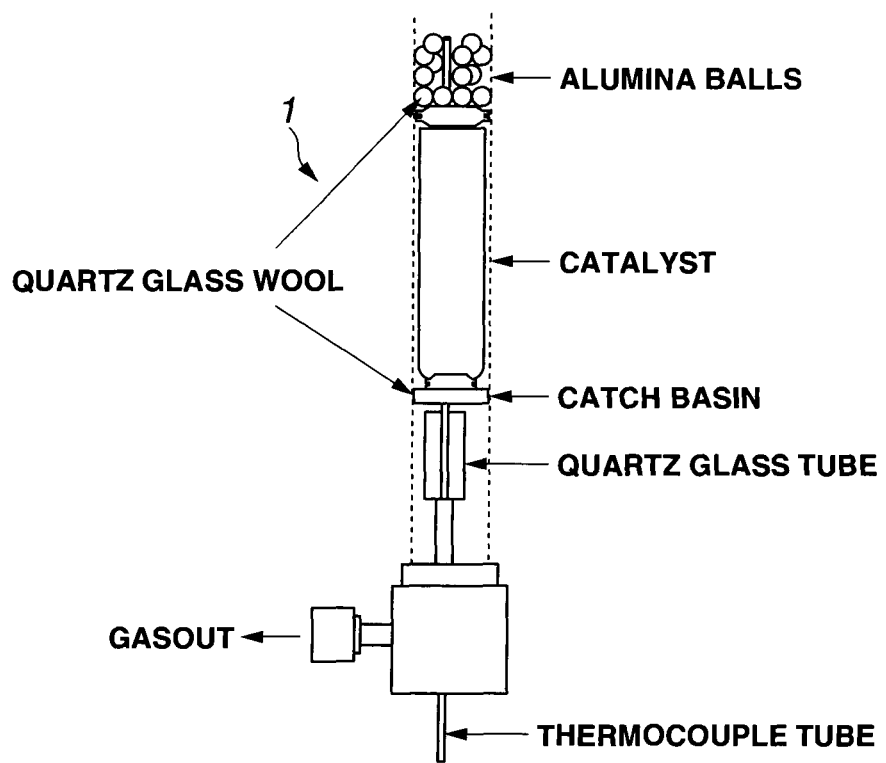
FIG. 13 is a schematic diagram of a fixed-bed flow reactor used to carry out an aromatization reaction for lower hydrocarbons, a catalyst according to the present invention being charged into the reactor.

A method for evaluating the catalysts of Comparative Examples and Examples will be discussed. As shown in FIG. 13, 14 g of a catalyst having a zeolite ratio of 82.50% and serving as a target for evaluation was charged into a reaction tube of a fixed-bed flow reactor, the tube having an internal diameter of 18 mm and produced in such a manner as to make a calorizing treatment on Inconel 800H's portion with which gas can be brought into contact. Then a reaction gas was supplied to the reaction tube under the conditions as shown in Table 1. More specifically, the catalyst was reacted with the reaction gas represented by 100CH$_4$ (methane)+3CO$_2$ (carbonic acid gas), under the conditions of: a reaction space velocity of 3000 ml/g-MFI/h (CH$_4$ gas flow base); a reaction temperature of 780° C.; a reaction time of 24 hours; and a reaction pressure of 0.3 MPa. During the reaction, a product analysis was conducted by using TCD-GC and FID-GC to examine a time variation in the methane conversion rate, the benzene formation rate, the naphthalene formation rate and the BTX formation rate.

The methane conversion rate, the benzene formation rate, the naphthalene formation rate and the BTX formation rate were defined as follows:

Methane conversion rate={("a flow rate of feedstock methane"–"a flow rate of unreacted methane")/"the flow rate of feedstock methane"}×100

Benzene formation rate="the number of nanomoles (nmol) of benzene produced from 1 g of the catalyst per second"

Naphthalene formation rate="the number of nanomoles (nmol) of naphthalene produced from 1 g of the catalyst per second"

BTX formation rate="the total number of nanomoles (nmol) of benzene, toluene and xylene produced from 1 g of the catalyst per second"

TABLE 1

| Items | Reaction condition |
| --- | --- |
| Charged amount of catalyst | 14 g |
| Ratio of zeolite | 82.50% |
| Feedstock gas | 100CH$_4$ (methane) + 3CO$_2$ (carbonic acid gas) |
| Reaction space velocity | 3000 ml/g - MFI/h (CH$_4$ gas flow base) |
| Reaction temperature | 780° C. |
| Reaction time | 24 hours |
| Reaction pressure | 0.3 MPa |

FIG. 1 shows time variations in methane conversion rate, provided concerning the catalysts of Comparative Examples 1 to 3 and Example 1, respectively, in which each of the catalysts was reacted with methane gas and carbonic acid gas according to the above-mentioned evaluation method. As apparent from this property plot that illustrates the time variations in methane conversion rate, the catalyst of Example 1 (loading silver and molybdenum and therefore indicated in FIG. 1 by Ag/Mo) was improved in activity life stability of the methane conversion rate as compared with conventional catalysts such as those of Comparative Example 1 (loading molybdenum singly and therefore indicated by Mo), Comparative Example 2 (loading cobalt and molybdenum and therefore indicated by Co/Mo) and Comparative Example 3 (loading iron and molybdenum and therefore indicated by Fe/Mo).

Figure 2:
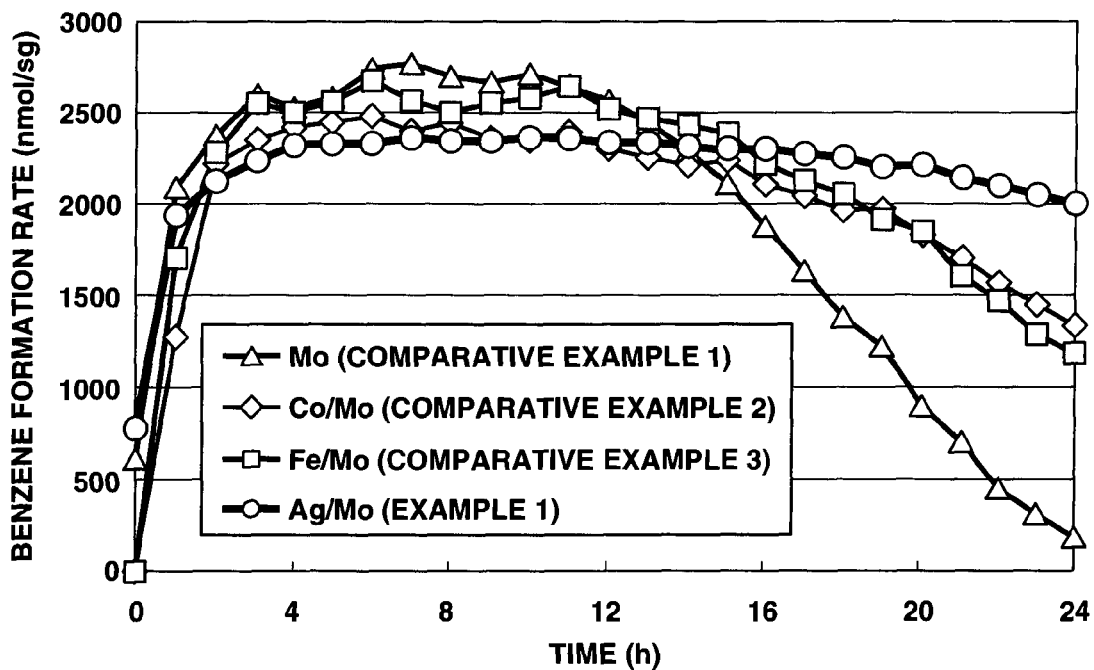
FIG. 2 shows time variations in benzene formation rate, the time variations being provided concerning catalysts of Comparative Example 1 (loading Mo singly), Comparative Example 2 (loading Co and Mo in one process step), Comparative Example 3 (loading Fe and Mo in one process step) and Example 1 (loading Ag and Mo in one process step), respectively, in which each of the catalysts was reacted with methane gas and carbonic acid gas.

FIG. 2 shows time variations in benzene formation rate, provided concerning the catalysts of Comparative Examples 1 to 3 and Example 1, respectively, in which each of the catalysts was reacted with methane gas and carbonic acid gas according to the above-mentioned evaluation method. As apparent from this property plot, the catalyst of Example 1 (Ag/Mo) was improved in activity life stability of the benzene formation rate as compared with conventional catalysts such as those of Comparative Example 1 (Mo), Comparative Example 2 (Co/Mo) and Comparative Example 3 (Fe/Mo).

Figure 3:
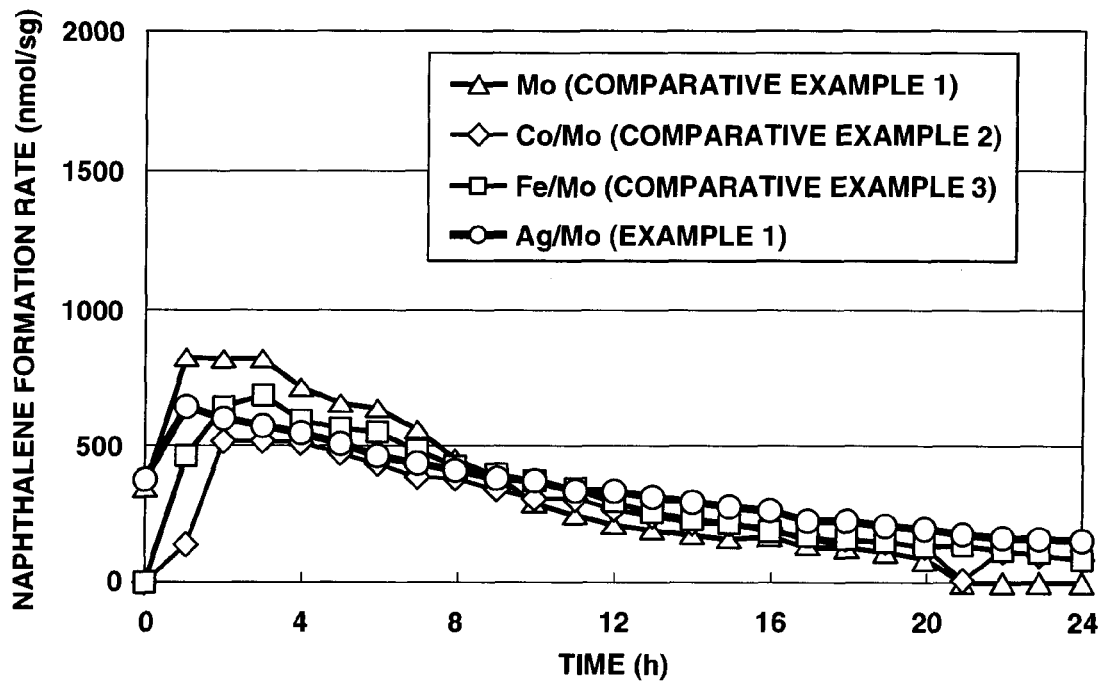
FIG. 3 shows time variations in naphthalene formation rate, the time variations being provided concerning catalysts of Comparative Example 1 (loading Mo singly), Comparative Example 2 (loading Co and Mo in one process step), Comparative Example 3 (loading Fe and Mo in one process step) and Example 1 (loading Ag and Mo in one process step), respectively, in which each of the catalysts was reacted with methane gas and carbonic acid gas.

FIG. 3 shows time variations in naphthalene formation rate, provided concerning the catalysts of Comparative Examples 1 to 3 and Example 1, respectively, in which each of the catalysts was reacted with methane gas and carbonic acid gas according to the above-mentioned evaluation method. As apparent from this property plot, the catalyst of Example 1 (Ag/Mo) was improved in activity life stability of the naphthalene formation rate as compared with conventional catalysts such as those of Comparative Example 1 (Mo), Comparative Example 2 (Co/Mo) and Comparative Example 3 (Fe/Mo).

Figure 4:
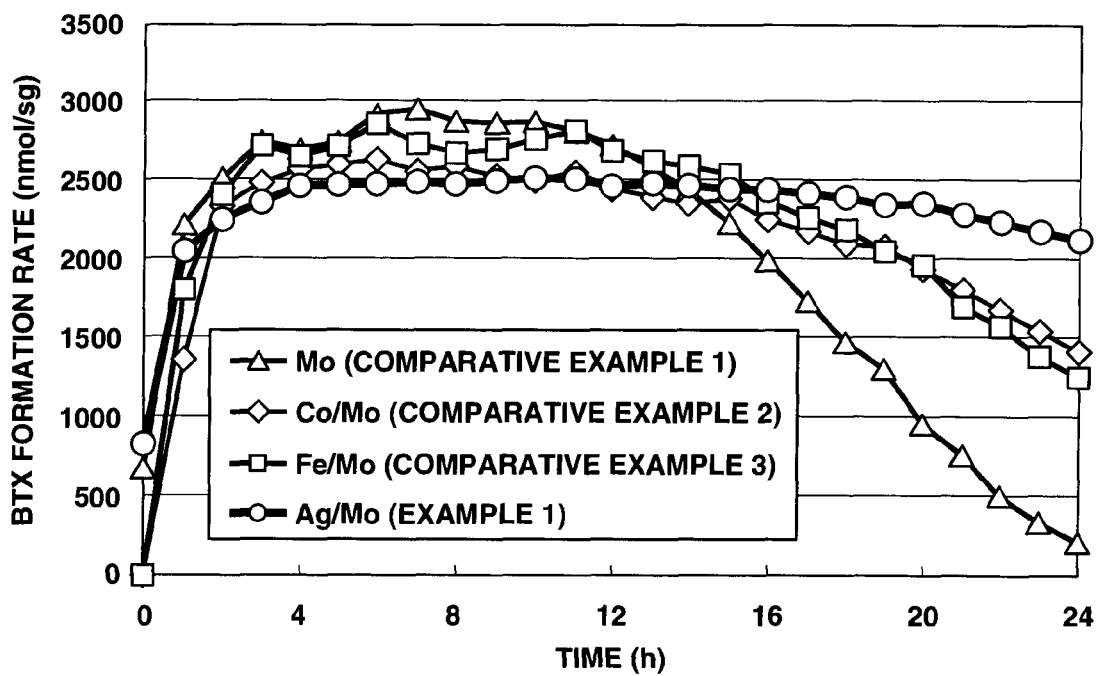
FIG. 4 shows time variations in BTX formation rate, the time variations being provided concerning catalysts of Comparative Example 1 (loading Mo singly), Comparative Example 2 (loading Co and Mo in one process step), Comparative Example 3 (loading Fe and Mo in one process step) and Example 1 (loading Ag and Mo in one process step), respectively, in which each of the catalysts was reacted with methane gas and carbonic acid gas.

FIG. 4 shows time variations in BTX formation rate, provided concerning the catalysts of Comparative Examples 1 to 3 and Example 1, respectively, in which each of the catalysts was reacted with methane gas and carbonic acid gas according to the above-mentioned evaluation method. As apparent from this property plot, the catalyst of Example 1 (Ag/Mo) was improved in activity life stability of the BTX formation rate as compared with conventional catalysts such as those of Comparative Example 1 (Mo), Comparative Example 2 (Co/Mo) and Comparative Example 3 (Fe/Mo).

Table 2 provides change rates of the methane conversion rate, the benzene formation rate, the naphthalene formation rate and the BTX formation rate. Each of the change rates is obtained from a characteristic value after 3 hour from an initiation of the reaction and that after 24 hour from the initiation of the reaction, the reaction being carried out in such a manner as to react each catalyst of Examples 2 to 5 with methane gas and carbonic acid gas in accordance with the above-mentioned evaluation method. It is confirmed from Table 2 that the catalysts of Examples 4 and 5 are particularly effective as compared with those of Examples 2 and 3 in terms of the change rates of the methane conversion rate, the benzene formation rate and the BTX formation rate.

TABLE 2

|  | Example 2 | Example 3 | Example 4 | Example 5 |
| --- | --- | --- | --- | --- |
| Mole ratio of Ag to Mo | Ag/Mo = 0.6 | Ag/Mo = 0.8 | Ag/Mo = 0.1 | Ag/Mo = 0.3 |
| Change rate of methane conversion rate (see Note 1) | 0.71 | 0.72 | 0.16 | 0.22 |
| Change rate of benzene formation rate | 0.99 | 0.99 | 0.20 | 0.42 |
| Change rate of BTX formation rate | 0.99 | 0.99 | 0.18 | 0.41 |

Note 1: Change rate = (a characteristic value (see Note 2) after 3 hour from an initiation of a reaction – that after 24 hour from the initiation of the reaction)/the characteristic value after 3 hour from the initiation of the reaction
Note 2: Characteristic value corresponds to the methane conversion rate (%), the benzene formation rate (nmol/sg) or the BTX formation rate (nmol/sg)

Figure 5:
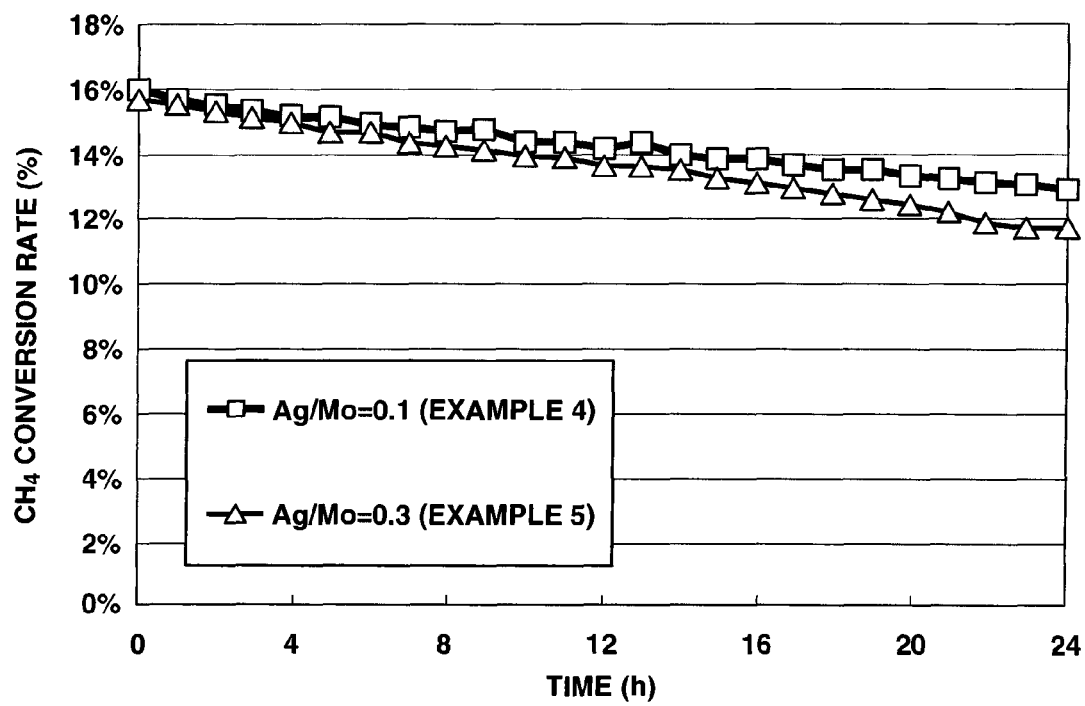
FIG. 5 shows time variations in methane conversion rate, the time variations being provided concerning catalysts of Example 4 (a mole ratio Ag/Mo of 0.1) and Example 5 (a mole ratio Ag/Mo of 0.3), respectively, in which each of the catalysts was reacted with methane gas and carbonic acid gas.

FIG. 5 shows time variations in methane conversion rate, the time variations being provided concerning the catalysts of Examples 4 and 5, respectively, in which each of the catalysts was reacted with methane gas and carbonic acid gas. As apparent from this property plot, the activity life stability of the methane conversion rate was improved when using the catalyst of Example 4 or 5.

Figure 6:
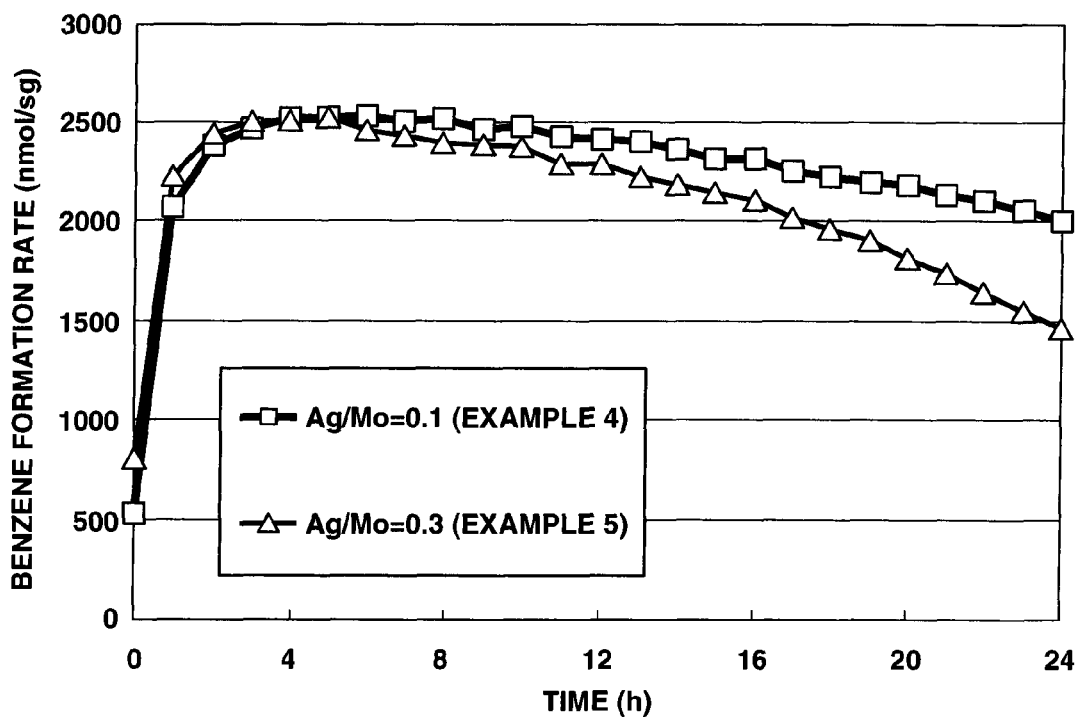
FIG. 6 shows time variations in benzene formation rate, the time variations being provided concerning catalysts of Example 4 (a mole ratio Ag/Mo of 0.1) and Example 5 (a mole ratio Ag/Mo of 0.3), respectively, in which each of the catalysts was reacted with methane gas and carbonic acid gas.

FIG. 6 shows time variations in benzene formation rate, the time variations being provided concerning the catalysts of Examples 4 and 5, respectively, in which each of the catalysts was reacted with methane gas and carbonic acid gas. As apparent from this property plot, the activity life stability of the benzene formation rate was improved when using the catalyst of Example 4 or 5.

Figure 7:
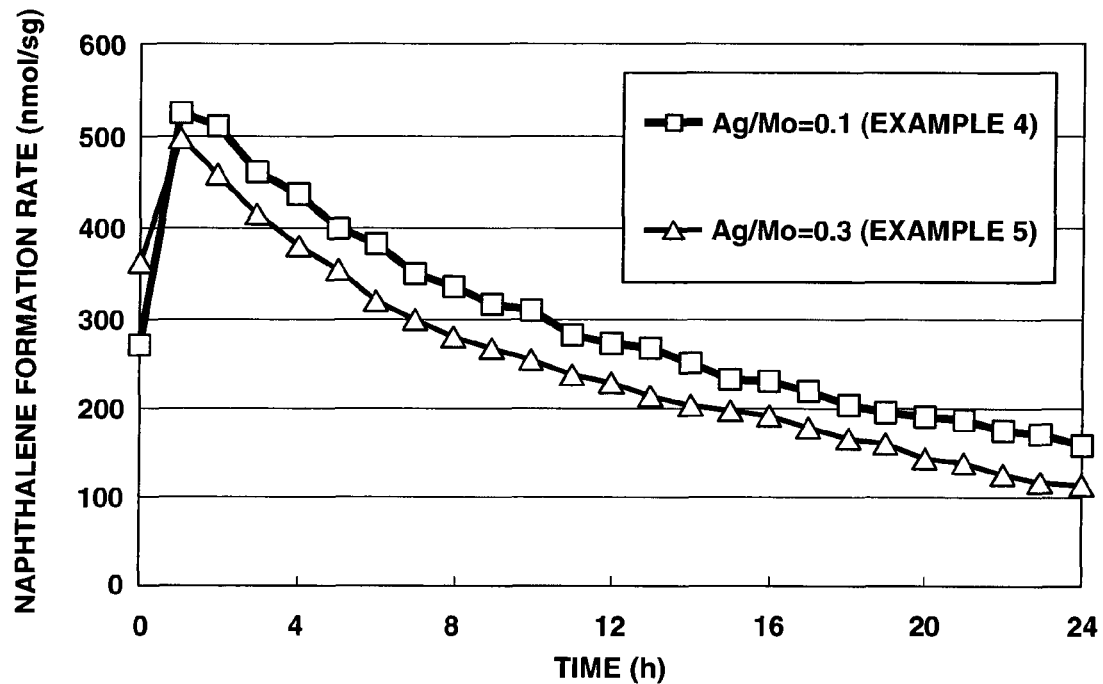
FIG. 7 shows time variations in naphthalene formation rate, the time variations being provided concerning catalysts of Example 4 (a mole ratio Ag/Mo of 0.1) and Example 5 (a mole ratio Ag/Mo of 0.3), respectively, in which each of the catalysts was reacted with methane gas and carbonic acid gas.

FIG. 7 shows time variations in naphthalene formation rate, the time variations being provided concerning the catalysts of Examples 4 and 5, respectively, in which each of the catalysts was reacted with methane gas and carbonic acid gas. As apparent from this property plot, the activity life stability of the naphthalene formation rate was improved when using the catalyst of Example 4 or 5.

Figure 8:
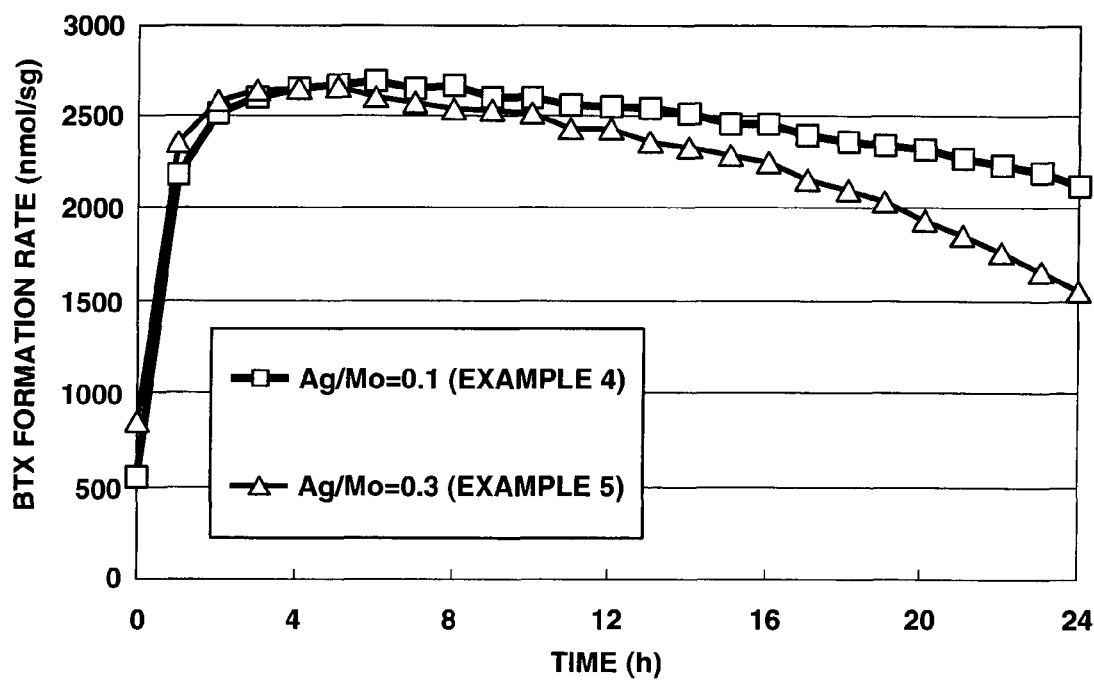
FIG. 8 shows time variations in BTX formation rate, the time variations being provided concerning catalysts of Example 4 (a mole ratio Ag/Mo of 0.1) and Example 5 (a mole ratio Ag/Mo of 0.3), respectively, in which each of the catalysts was reacted with methane gas and carbonic acid gas.

FIG. 8 shows time variations in BTX formation rate, the time variations being provided concerning the catalysts of Examples 4 and 5, respectively, in which each of the catalysts was reacted with methane gas and carbonic acid gas. As apparent from this property plot, the activity life stability of the BTX formation rate was improved when using the catalyst of Example 4 or 5.

From the above results of Examples 1 to 5, it is found that the activity life stability is improved in terms of the methane conversion rate, the benzene formation rate and the naphthalene formation rate, when a catalyst for aromatizing lower hydrocarbons is formed by loading silver in addition to molybdenum as a second metal component on metallosilicate and when the catalyst is reacted with lower hydrocarbons and carbonic acid gas. Further, it is found that the formation rate of BTX (useful components such as benzene and toluene) is stabilized. It is particularly found that silver having a mole ratio of from 0.01 to 0.3 to molybdenum makes the methane conversion rate more stable and reliably improves the catalyst in activity life stability.

Figure 9:
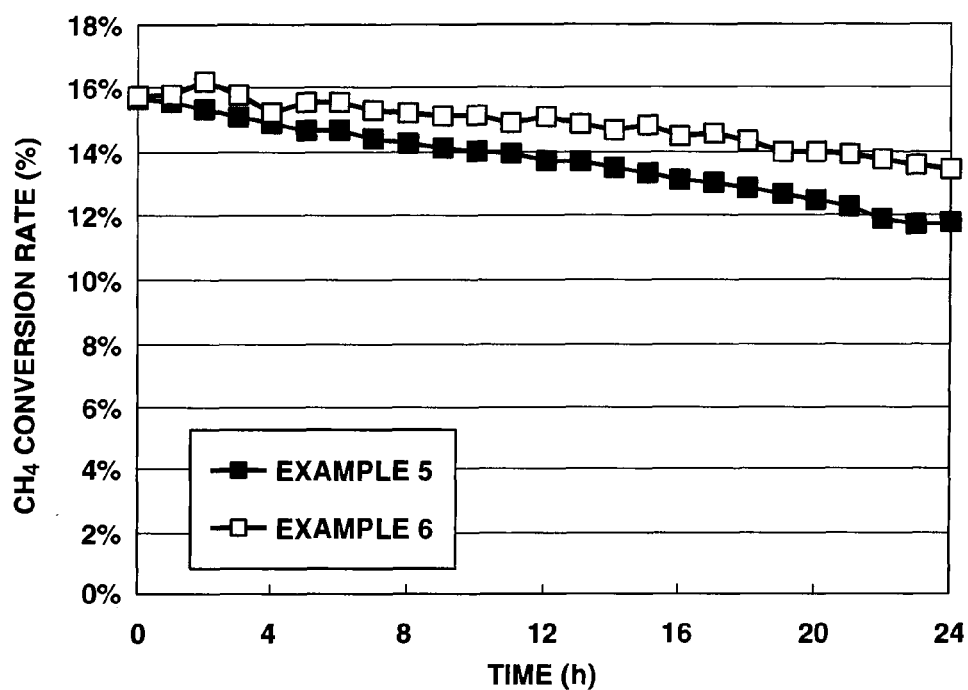
FIG. 9 shows time variations in methane conversion rate, the time variations being provided concerning catalysts of Examples 5 and 6, respectively, in which each of the catalysts was reacted with a carbonic acid gas-containing methane gas having a mole ratio of methane to carbonic acid gas (carbon dioxide) of 100:3.

Additionally, FIG. 9 shows time variations in methane conversion rate, the time variations being provided concerning the catalysts of Examples 5 and 6, respectively, in which each of the catalysts was reacted with the carbonic acid gas-containing methane gas. It is apparent, from a comparison of time variation in methane conversion rate between the reaction using the catalyst of Example 6 and that using the catalyst of Example 5, the catalyst of Example 6 on which the modification with silane (or silane-modification) was carried out was more improved in activity life stability of the benzene formation rate than that of Example 5 on which the silane-modification was not carried out.

Figure 10:
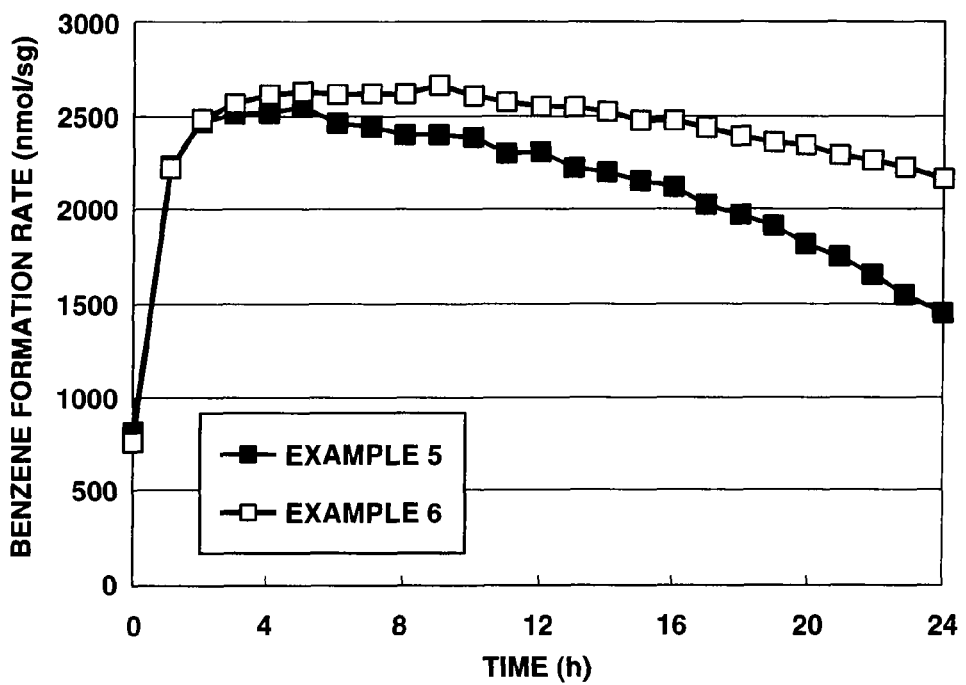
FIG. 10 shows time variations in benzene formation rate, the time variations being provided concerning catalysts of Examples 5 and 6, respectively, in which each of the catalysts was reacted with a carbonic acid gas-containing methane gas having a mole ratio of methane to carbonic acid gas (carbon dioxide) of 100:3.

FIG. 10 shows time variations in benzene formation rate, the time variations being provided concerning the catalysts of Examples 5 and 6, respectively, in which each of the catalysts was reacted with the carbonic acid gas-containing methane gas. As apparent from this property plot, the catalyst of Example 6 on which the modification with silane (or silane-modification) was carried out was more improved in activity life stability of the benzene formation rate than that of Example 5 on which the silane-modification was not carried out.

Figure 11:
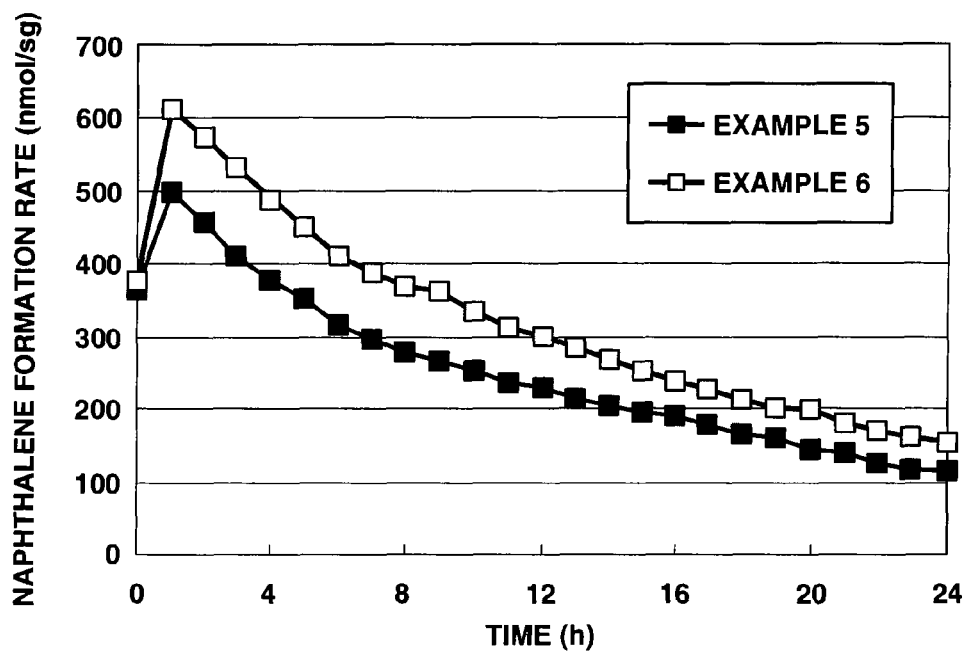
FIG. 11 shows time variations in naphthalene formation rate, the time variations being provided concerning catalysts of Examples 5 and 6, respectively, in which each of the catalysts was reacted with a carbonic acid gas-containing methane gas having a mole ratio of methane to carbonic acid gas (carbon dioxide) of 100:3.

FIG. 11 shows time variations in naphthalene formation rate, the time variations being provided concerning the catalysts of Examples 5 and 6, respectively, in which each of the catalysts was reacted with the carbonic acid gas-containing methane gas. As apparent from this property plot, the catalyst of Example 6 on which the modification with silane (or silane-modification) was carried out was more improved in activity life stability of the naphthalene formation rate than that of Example 5 on which the silane-modification was not carried out.

Figure 12:
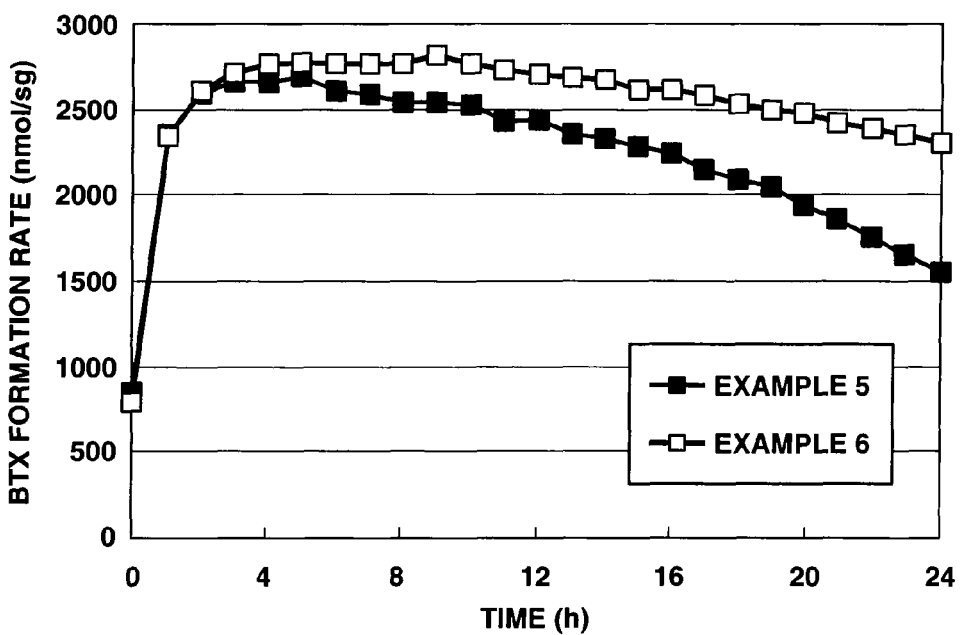
FIG. 12 shows time variations in BTX formation rate, the time variations being provided concerning catalysts of Examples 5 and 6, respectively, in which each of the catalysts was reacted with a carbonic acid gas-containing methane gas having a mole ratio of methane to carbonic acid gas (carbon dioxide) of 100:3.

FIG. 12 shows time variations in BTX formation rate, the time variations being provided concerning the catalysts of Examples 5 and 6, respectively, in which each of the catalysts was reacted with the carbonic acid gas-containing methane gas. As apparent from this property plot, the catalyst of Example 6 on which the modification with silane (or silane-modification) was carried out was more improved in activity life stability of the BTX formation rate than that of Example 5 on which the silane-modification was not carried out.

As discussed above, the catalyst according to the present invention, formed by loading molybdenum and silver on metallosilicate after modifying the metallosilicate with silane, can improve the activity life stability of the methane conversion rate. It is, therefore, allowed to stably obtain the benzene formation rate, the naphthalene formation rate and the BTX (useful components such as benzene and toluene) formation rate. Particularly in a case of loading silver and molybdenum in one process step on metallosilicate after adding 0.5 wt % of the silane compound such that a mole ratio of silver to molybdenum was 0.3, the activity stability of the methane conversion rate is improved thereby providing a stable BTX (useful components such as benzene and toluene) formation rate. The mole ratio is not limited to 0.3, and is effective even if not higher than 0.3. More specifically, it is experimentally verified that a mole ratio within a range from 0.01 to 0.8 can provide the same effects as those of the above-mentioned Examples.

In the above-mentioned Examples, ZSM-5 is employed as metallosilicate on which a metal component is loaded; however, even if MCM-22 is employed, the same effects as those of Examples are provided. Further, in the above-mentioned Examples a loaded amount of molybdenum is 6% by weight relative to a total amount of the catalyst which has undergone calcination; the same effects as those of Examples are provided as far as a loaded amount of molybdenum is within a range of from 2 to 12% by weight relative to a total amount of the catalyst which has undergone calcination. Further, in the above-mentioned Examples the silane compound is added in an amount of 0.5% by weight relative to the total amount of the catalyst which has undergone calcination; however, the same effects as those of Examples are provided as far as the amount is less than 2.5 wt %. Furthermore, in the above-mentioned Examples the catalyst is reacted with the reaction gas having a mole ratio of methane to carbonic acid gas (carbon dioxide) of 100:3 thereby producing aromatic compounds in the evaluation method; however, the same effects as those of Examples are provided even if an addition amount of the carbonic acid gas is within a range of from 0.5 to 6% relative to a total of the reaction gas.

The invention claimed is:

1. A process for producing an aromatic compound, comprising the steps of:
   loading molybdenum and silver on a substrate formed of metallosilicate, thereby producing a catalyst; and
   reacting the catalyst with a reaction gas containing a lower hydrocarbon and a carbonic acid gas, thereby producing the aromatic compound,
   wherein the metallosilicate is porous and has a pore diameter of 4.5 to 6.5 Angstrom.

2. A process for producing an aromatic compound, as claimed in claim 1, wherein the carbonic acid gas is added in an amount ranging from 0.5 to 6% relative to a total amount of the reaction gas.

3. A process for producing an aromatic compound, as claimed in claim 1, wherein the metallosilicate includes one of ZSM-5 and MCM-22.

4. A process for producing an aromatic compound, as claimed in claim 1, wherein a concentration of the loaded molybdenum after calcination is within a range of from 2 to 12% by weight relative to the substrate, while a mole ratio of the loaded silver to 1 mol of the molybdenum is within a range of from 0.01 to 0.3.

5. A process for producing an aromatic compound, as claimed in claim 1, wherein a calcination is made after loading the molybdenum and the silver on the metallosilicate, at a temperature of from 400 to 700° C.

6. A process for producing an aromatic compound, comprising the steps of:

modifying zeolite formed of metallosilicate with a silane compound larger than a pore of the metallosilicate in molecular diameter, the pore diameter of the metallosilicate being 4.5 to 6.5 Angstrom, the silane compound having an amino group and a straight-chain hydrocarbon group, the amino group being able to selectively react with the zeolite at a Bronsted acid point of the zeolite;

loading molybdenum and silver on the zeolite thereby producing a catalyst; and reacting the catalyst with a reaction gas containing a lower hydrocarbon and a carbonic acid gas, thereby producing the aromatic compound.

7. A process for producing an aromatic compound, as claimed in claim 6, wherein the carbonic acid gas is added in an amount ranging from 0.5 to 6% relative to a total amount of the reaction gas.

* * * * *